United States Patent [19]

Rodicio et al.

[11] Patent Number: 5,612,219

[45] Date of Patent: Mar. 18, 1997

[54] ANTI-FOAM DEVICE FOR A BIOREACTOR

[75] Inventors: Ignacio Rodicio, Pully; Gerard Mignot, Lavigny, both of Switzerland

[73] Assignee: Applied Research Systems Ars Holding N.V., Netherlands

[21] Appl. No.: 557,134

[22] PCT Filed: Jun. 11, 1993

[86] PCT No.: PCT/EP93/01488

§ 371 Date: Dec. 8, 1995

§ 102(e) Date: Dec. 8, 1995

[87] PCT Pub. No.: WO94/29432

PCT Pub. Date: Dec. 22, 1994

[51] Int. Cl.[6] ................................................ C12M 3/00
[52] U.S. Cl. .................... 435/301.1; 435/286.7; 422/224; 422/225
[58] Field of Search ........................... 435/286.7, 301.1; 422/224, 225

[56] References Cited

U.S. PATENT DOCUMENTS 4,373,024  2/1983  Hunt .................................... 435/41

FOREIGN PATENT DOCUMENTS 1480466  6/1968  Australia.
0529089  3/1993  European Pat. Off. ......... C12M 1/06

Primary Examiner—David A. Redding
Attorney, Agent, or Firm—Ostrolenk, Faber, Gerb & Soffen, LLP

[57] ABSTRACT

An anti-foam device for a bioreactor is provided consisting of a perforated plate, made by hydrophobic material, which rotates at the surface of the liquid culture medium contained in the bioreactor vessel, the perforated plate being perpendicular to an inclination from 45 to 90 degrees in respect of the surface of the culture medium.

28 Claims, 1 Drawing Sheet

ANTI-FOAM DEVICE FOR A BIOREACTOR

TECHNICAL FIELD

The present invention refers to an anti-foam device particularly suitable to break the foam which is formed at the surface of a liquid culture medium contained in a stirred-tank bioreactor equipped with an impeller for stirring and with sparging gas means.

BACKGROUND OF THE INVENTION

In stirred-tank bioreactors used for laboratory-scale or pilot-scale mammalian cell culture, foam generation due to the injection of gas containing oxygen in the reactor is one of the more critical problems which remain to be solved: in fact, accumulation of foam at the culture medium surface decreases the gas transfer rate (oxygen from air to culture medium and $CO_2$ from culture medium to air), which is a relevant parameter for a correct and continuous growth of the mammalian cells.

If the gas transfer due to surface aeration is unable to supply the whole amount of oxygen required for the cell growth, in some cases direct sparging of air into the culture medium is used, but said direct sparging of air involves foam production which in turn reduces the surface air/liquid gas transfer rate: it is known that the increased oxygen flow rate required to maintain the desired oxygen concentration in the bioreactor culture medium has (or could have) detrimental effects on cell viability.

The production of foam due to gas sparging is particularly detrimental if said mammalian cells are grown on microcarriers as the air sparging bubbles carry along the microcarriers making them float at the culture medium surface where they remain trapped on a foam bubble network: this phenomena leads to a decrease of the amount of microcarriers and of the cell density in the reactor and consequently so a decrease of the overall reactor productivity.

Formation of very large cell and microcarrier aggregates can lead to non-homogeneous culture and makes cleaning of the bioreactor more difficult at the end of a run.

The solution presently used to solve the foam problem provides that an anti-foam chemical product (normally a silicone emulsion made, for example, of 30% Simethicone USP plus 14% stearate emulsifier and 0.075% sorbic acid in water) is added to the liquid, but such a solution creates several problems, may have some toxic effects on some cell lines and reduce recombinant protein expression by genetically engineered cells.

Over the last years the use of a mechanical surface aerator had been investigated as a different approach to the problem of reaching a proper surface aeration without gas sparging (or at least with a reduced gas sparging), so avoiding or at least limiting the production of foam.

W. S. HU and al. (Biotechnol. Bioeng. Vol. XXVIII, pp 122–125, 1986) disclose a mechanical surface aerator mounted on the same shaft of the impeller to improve gas transfer from the gas/liquid interface in the liquid.

Said surface aerator is particularly suitable if applied to small size laboratory bioreactors and increases turbulence of the liquid surface so improving surface aeration and reducing the need of gas sparging: as a consequence, a reduced foam production occurs.

As the same Authors say, one use of a surface aerator will surely not solve oxygen transfer problems in large scale operations; however, on any scale in which surface aeration contributes a significant extent of the oxygen transferred to the culture, a surface aerator will certainly have an enhancement effect.

EP-A-0 257 750 refers to a bioreactor equipped with a surface aerator made of a metallic screen and moved by suitable moving means: said screen is on a float allowing it to stay at or just below the surface of the liquid.

The surface of the screen is parallel to that of the liquid and its rotation generates turbulence at the surface of the liquid, thus improving the oxygen transfer rates.

The Applicant discovered that when a perforated plate made of an hydrophobic material rotates at the surface of a liquid filled in a bioreactor in a perpendicular position (or with an inclination from 45° to 90°) in respect to said surface and partially immersed into said liquid, a surprising foam breaking effect occurs. Moreover, said anti-foam device allows a significant improvement of the surface aeration rate of the liquid by increasing the gas exchange rate at the gas/liquid interface.

On a preferred embodiment, said hydrophobic perforated plate is held by a stainless steel support.

DISCLOSURE OF THE INVENTION

The present invention refers to an anti-foam device for a bioreactor containing a liquid culture medium and equipped with an impeller for stirring and with sparging gas means.

Said anti-foam device consists of a perforated plate, made by hydrophobic material, which rotates at the surface of the liquid culture medium: said plate is fixed in a perpendicular position (or with an inclination from 45° to 90°) in respect of the culture medium surface to the shaft of the impeller and is partially immersed into said liquid culture medium.

The rotation speed of the perforated plate, corresponding to that of the shaft, is in the range from 10 to 100 rpm and preferably from 30 to 50 rpm.

Said perforated plate is held by a metal support (preferably a stainless steel support) linked to the impeller shaft through sliding means (for example a screwed-up collar) whose position can be adjusted to have the plate sweeping the surface of the culture medium: the length of the portion of said plate which is immersed in the culture medium may vary from 1 to 10 mm (preferably from 1 to 7.5 mm).

Said perforated plate is cut from a sheet of hydrophobic material having a thickness in the range of 1 to 5 mm (preferably from 1.5 to 4 mm) and square or rectangular shaped holes are pierced therein; piercing of round shaped holes, even if possible, is normally avoided.

Suitable hydrophobic materials for the building of the perforated plate of the invention are: polymers such as silicone, polyamides, polypropylene, polyesters, fluorinated plastomers and elastomers, synthetic rubbers (isoprene, butadiene etc.) and metallic nets coated with the above mentioned polymers.

The size of the square holes is in the range from 1×1 mm to 10×10 mm (preferably from 5×5 mm to 8×8 mm: two or more square holes (even of different sizes, if needed) could be combined to generate said rectangular holes.

The size (thickness of the layer of hydrophobic material surrounding a square or rectangular hole) of the framework of said plate is in the range from 1 to 5 mm (preferably from 1 to 3 mm); the framework/hole ratio is in the range from 15 to 80% and preferably from 20 to 60%.

Said framework must have sharp angles in order to get an optimal foam breaking effect.

The overall shape of said perforated plate is square or rectangular and its size is adapted to the type and to the internal size of the reactor where the anti-foam device is installed: the height of the perforated plate is in the range from 5 to 50 cm (preferably from 5 to 15 cm).

An anti-foam device according to the invention is so effective that the foam breaking effect occurs even if the perforated plate sweeps only a portion of the total liquid/air surface: in fact said foam breaking effect occurs even if the ratio between the surface swept by the perforated plate and the total liquid/air surface is up to 30%, while if said ratio exceeds 80% no improvement of said foam breaking effect occurs.

Preferably the above ratio should be between 40% and 60%.

If the above mentioned bioreactor further contains a spinfilter, said perforated plate is divided in two separate sections, each of which is fixed in a perpendicular position (or with an inclination from 45° to 90°) in respect of the culture medium surface on the opposite sides of said spinfilter and is partially immersed into said liquid culture medium.

The rotation speed of said perforated plate, corresponding to that of the spinfilter, is in the range from 10 to 100 rpm and preferably from 30 to 50 rpm.

The presence of the spinfilter reduces the overall length of the two-section perforated wall, but however the foam breaking effect occurs by maintaining the ratio between the surface swept by the two-section perforated plate and the total liquid/air surface inside the previously said range.

BRIEF DESCRIPTION OF DRAWINGS

The invention will be better described with reference to the particular embodiments illustrated in the enclosed drawings where:

FIGS. 1 and 2 show schematically two types of stirred-tank bioreactors, known in the art, which are equipped with an anti-foam device realised according to the invention, while FIG. 3 shows an enlarged view of the anti-foam device shown in FIG. 2: in the figures only the essential features of said bioreactors, useful for the present description, are shown.

No gas sparging means, normally used in said types of bioreactors, are shown in the figures in order to give a clearer graphic form to the drawings.

Moreover, as far as possible corresponding features has been evidenced in all figures through the same reference numbers.

DETAILED DESCRIPTION OF INVENTION

Figure 1:
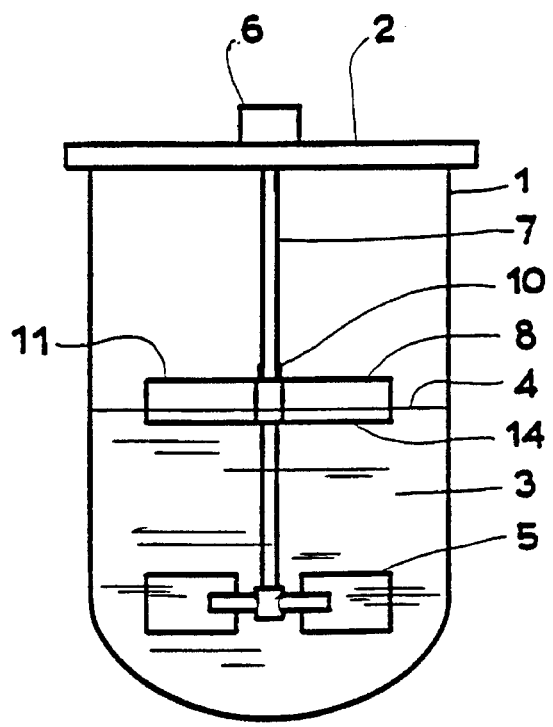
FIG. 1 shows schematically a bioreactor comprising a first embodiment of an anti-foam device realised according to the invention.

FIG. 1 shows a culture vessel 1, closed by a lid 2 and partially filled with a liquid culture medium 3 as to the air/liquid interface 4: an impeller 5, immersed into the culture medium 3, is clockwise (or counterclockwise) rotated by the driver 6 through the shaft 7.

A perforated plate 8 made of a silicone polymer is rotating at the surface 4 of said culture medium 3: the surface of said perforated plate 8 is perpendicular to (or with an inclination from 45° to 90° in respect of) said culture medium surface 4 and is partially immersed into said culture medium 3.

Said perforated plate 8 is held by a metal support 11 linked to the impeller shaft 7 through a screwed-up collar 10 whose position can be adjusted to have the perforated plate 8 sweeping the surface 4 of the culture medium 3.

Said perforated plate 8 is cut from a silicone polymer sheet and square shaped holes are pierced therein; the framework 13 (evidenced in FIG. 3) of said perforated plate 8 has sharp angles in order to get an optimal foam breaking effect.

The overall shape of said perforated plate 8 is square or rectangular and its size is adapted to the type, to the shape and to the internal size of the reactor where the anti-foam device is installed.

Figure 2:
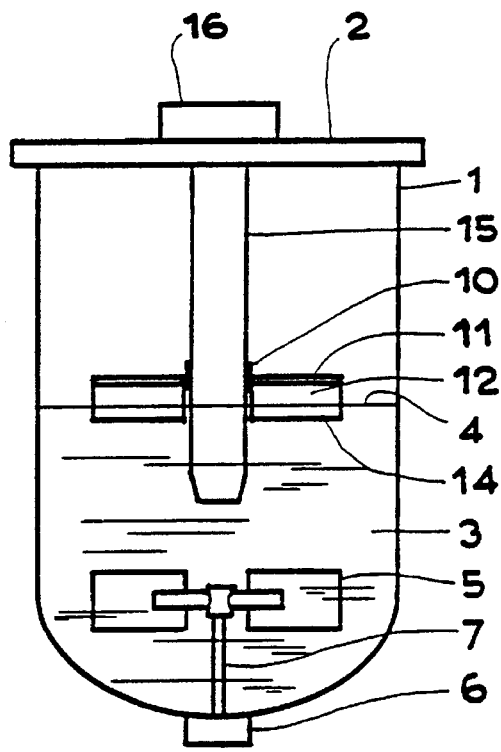
FIG. 2 shows schematically a bioreactor comprising a spinfilter and equipped with a second embodiment of an anti-foam device realised according to the invention.

FIG. 2 shows schematically a second bioreactor equipped with a second embodiment of an anti-foam device: the main difference between said second bioreactor and the first one is that said second bioreactor comprises a spinfilter 15, moved by the relevant drive 16, to which said anti-foam device is linked through the screwed-up collar 10.

So, in FIG. 2 are shown the culture vessel 1, closed by the lid 2 and partially filled with the culture medium 3 as to the air/liquid interface 4; the impeller 5, immersed into the culture medium 3 and clockwise (counterclocwise) rotated by the driver 6 through the shaft 7 and the spinfilter 15, anticlockwise (clockwise) rotated by the driver 16, to which the anti-foam device of the invention is linked.

The spinfilter 15, whose symmetry axis coincides with that of the vessel 1, has a size which cannot be neglected: so, in the anti-foam device shown in FIG. 2 the perforated plate 8 of FIG. 1 is divided in two equal sections 12, each of which is held by a metal support 11 linked to the spinfilter 15 through the screwed-up collar 10 whose position can be adjusted to have the sections 12 sweeping the surface 4 of the culture medium 3.

As had been evidenced above with reference to FIG. 1, each of said sections 12 is cut from a silicone polymer sheet and square shaped holes are pierced therein.

The framework 13 (evidenced in FIG. 3) of each of said sections 12 has sharp angles in order to get an optimal foam breaking effect.

The overall shape of each of said sections 12 of the perforated plate 8 is square or rectangular and its size is adapted to the type, to the shape and to the internal size of the reactor where the anti-foam device is installed.

Figure 3:
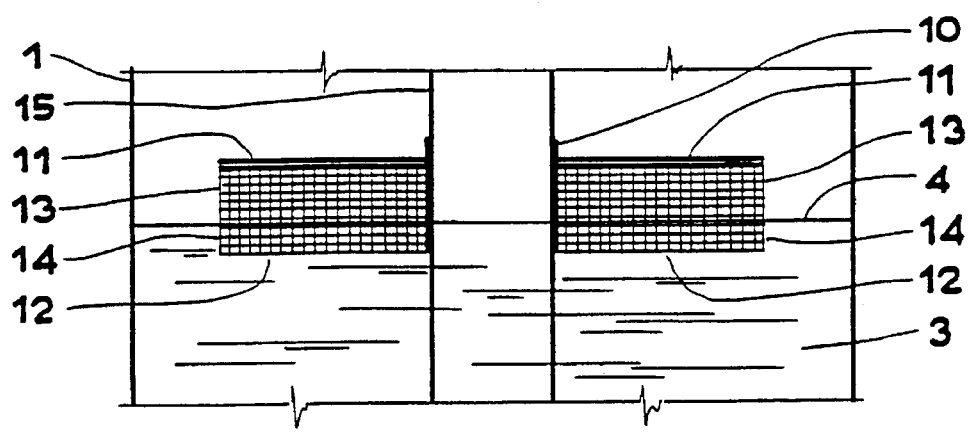
FIG. 3 shows, in an enlarged view, the portion of the bioreactor shown in FIG. 2 comprising said anti-foam device.

FIG. 3 shows, in an enlarged view, the portion of the bioreactor shown in FIG. 2 comprising said anti-foam device and, in particular, the two sections 12 held to the relevant supports 11 linked to the spinfilter 15 through the screwed-up collar 10.

An anti-foam device according to the invention will be better described with reference to the following non-limiting examples.

EXAMPLE 1

A test was made by filling with water a known type of bioreactor (75 liters MBR, internal diameter=310 mm, ratio height/diameter=3/1) like that shown in the FIGS. 2 and 3, by adding into said bioreactor an anti-foam chemical product (a silicone emulsion made of 30% Simethicone USP plus 14% stearate emulsifier and 0.075% sorbic acid in water) and by measuring the oxygen mass transfer rates (KLa).

The operative parameters of the bioreactor were the following ones:
Bioreator working volume: 50 L
Liquid: water
Bottom impeller: marine impeller 3 blades, angle 30°
Bottom stirring speed (Clockwise): 40 rpm
Spinfilter speed (Counterclockwise): 50 rpm
No draught-tube
Number of spargers: 6
Sparger porosity: 0.50 micrometers
Oxygen flow rate: 40 ml/mn
Bioreactor head-space over pressure: 200 mB
Bioreactor temperature: 37° C.
Air flow rate in reactor head space: 2 Normal l/mn
Dissolved oxygen determination: Polarographic PO2 probe INGOLD
KLa determination method: PO2 probe method The test has evidenced that the addition of 1.50 ppm of said anti-foam product to water reduces KLa from $7.21 \text{ exp-4 s-1}$ to $3.94 \text{ exp-4 s-1}$.

EXAMPLE 2

Repeating the test of example 1 by using the same reactor and the same operative conditions of the example 1 but by substituting the water with a production medium (IMDM/HAM F12+1% FBS), we have evidenced that the addition of 1.50 ppm of said anti-foam product to said medium reduces KLa from $1.16 \text{ exp-3 s-1}$ to about $1.00 \text{ exp-3 s-1}$.

From the test results of examples 1 and 2 it can be concluded that the addition of the above anti-foam product reduces significantly oxygen transfer rates, increasing therefore the oxygen flow rates needed to maintain the required oxygen concentration in the bioreactor.

EXAMPLE 3

To perform the tests on the efficacy of the anti-foam device of the invention, we used the bioreactor of example 1 (75 liters MBR, internal diameter=310 mm, ratio height/diameter=3/1) equipped with a spinfilter and with a silicone perforated plate divided in two equal sections linked to opposite sides of the spinfilter.

The characteristics of each section of the perforated plate are:
Thickness of the silicone sheet: 2 mm
Thickness of the plane framework: 1.5 mm
Length of each section: 70 mm
Height of each section: 70 mm
Length of the section portion immersed in the liquid: 7.5 mm
Plate framework: having sharp angles
Size of the square holes: 7×7 mm The plate framework/square holes ratio is of about 22.6%.

The surface of the liquid/air interface was 75 480 $mm^2$ and the surface of the liquid/air interface swept by each section was 39 586 $mm^2$, so that the ratio between the surface swept by each section and the total liquid/air surface was 52.4%

We have performed the test two times, at first without foam breaking device, with foam breaking device: test results evidenced that in water without foam breaking device KLa for oxygen is $7.21 \text{ exp-4 s-1}$ while with foam breaking device it is $7.95 \text{ exp-4 s-1}$.

EXAMPLE 4

We repeated the tests of example 3 by using the same reactor and the same operative conditions of said example but by substituting the water with the production medium (IMDM/HAM F12+1% FBS): test results evidenced that in production medium the effect is even more significant while KLa increases from $1.16 \text{ exp-3 s-1}$ without foam breaking device up to $1.52 \text{ exp-3 s-1}$ with foam breaking device.

From the test results of examples 3 and 4 it can be concluded that the increase of KLa, which is mostly related to the improved surface aeration and incorporation of oxygen at the interface liquid/air of the bioreactor head space due to turbulences generated by the foam breaking device at said interface, is in the range of 20 to 30%, which is highly significant; the above mentioned KLa determination method allows carrying out of very accurate and reproducible measures.

EXAMPLE 5

To the purpose of comparing the efficacy of the anti-foam device of the invention with the addition of an anti-foam emulsion in a liquid culture medium, we performed further tests by using the same equipment and operational parameters used in the example 3 but with the following differences:
Cell line: CHO A2 r-hFSH producing cell line
Cell culture media: growth, rinsing and production medium (IMDM/HAM F12 supplemented with respectively 5%, 0.5% and 1% FBS)
Air flow rate in reactor head space: 1.5 Normal l/mn
pH: 7.20 to 7.00 during growth phases 6.80 during rinsing and production phases The tests in the presence of the anti-foam emulsion are performed by eliminating the anti-foam device and by adding to the culture medium 7.5 to 10 g of the known silicone emulsion (30% Simethicone USP plus 14% stearate emulsifier and 0.075% sorbic acid in water) so to avoid foam generation during a standard run of 37 days.

During standard runs performed without using the foam-breaking device, the foam layer is 2 to 3 cm height at the culture medium surface and a discontinuous addition of anti-foam emulsion is necessary to limit the foam thickness at the level of 2 to 3 cm.

During test runs performed with the foam-breaking device, foam generation due to gas sparging has been very small if compared with the standard runs, evidencing that the two-section silicone perforated plate linked to the spinfilter have been very efficient to destroy foam; furthermore no microcarrier have been trapped in the foam.

Only a thin foam layer of about 1 cm tends to accumulate at the periphery of the culture medium interface in the bioreactor; the surface swept by the two-section silicone plates was free by foam and free of floating microcarriers.

In conclusion, no detrimental effects to the cells due to the Applicant's anti-foam device have been noticed duping the tests; so, turbulences generated by the two-section silicone plate at the gas/liquid interface increase surface aeration without altering cell attachment.

We claim:
1. An anti-foam device for a bioreactor containing a liquid culture medium and equipped with an impeller for stirring and with sparging gas means, comprising:
   a perforated plate constructed of a hydrophobic material for reducing foam on the surface of the culture medium, said plate being fixed to a shaft of said impeller with an inclination from 45 to 90 degrees in respect of the culture medium surface and being partially immersed into said liquid culture medium.

2. Anti-foam device according to claim 1, wherein said perforated plate is fixed to said shaft of said impeller with an inclination of 90° in respect of said culture medium surface.

3. Anti-foam device according to claim 1, wherein the length of the portion of said perforated plate immersed in said liquid culture medium is in the range from 1 to 10 mm.

4. Anti-foam device according to claim 1, wherein said perforated plate is realised through a silicone sheet held by a metal support linked to said shaft of said impeller through a sliding means whose position can be adjusted to have said perforated plate sweeping said surface of said liquid culture medium.

5. Anti-foam device according to claim 4, wherein said metal support is a stainless steel support.

6. Anti-foam device according to claim 4, wherein said sliding means are realised through a screwed up collar.

7. Anti-foam device according to claim 1, wherein said perforated plate has a square or a rectangular shape.

8. Anti-foam device according to claim 1, wherein said perforated plate is a pierced plate made of a silicone polymer, the thickness of said plate being in the range from 1 to 5 mm.

9. Anti-foam device according to claim 1, wherein the perforations of said perforated plate has sharp angles.

10. Anti-foam device according to claim 1, wherein the holes of said perforated plate have a square or rectangular shape.

11. Anti-foam device according to claim 10, wherein the size of said square holes is in the range from 1×1 mm to 10×10 mm.

12. Anti-foam device according to claim 1, wherein said hydrophobic material is selected from the group consisting of hydrophobic polymers and of metallic nets coated with the above mentioned polymers.

13. Anti-foam device according to claim 12, wherein said hydrophobic polymers include silicone, polyamides polypropylene, polyesters, fluorinated plastomers and elastomers, synthetic rubber.

14. Anti-foam device for a bioreactor containing a liquid culture medium and an impeller for stirring, a spinfilter, and sparging gas means, consisting of:
  a perforated plate which rotates at the surface of the liquid culture medium and is constructed of hydrophobic material and is divided in two separate sections, each section being fixed to opposite sides of the spinfilter with an inclination from 45 to 90 degrees in respect of the culture medium surface and being partially immersed into said culture medium.

15. Anti-foam device according to claim 14, wherein said sections are fixed to the opposite sides of said spinfilter with an inclination of 90° in respect of said culture medium surface.

16. Anti-foam device according to claim 14, wherein each of said sections is constructed of a silicone plate held by a metal support linked to said spinfilter through sliding means whose position can be adjusted to have said sections sweeping said surface of said liquid culture medium.

17. Anti-foam device according to claim 16, wherein said metal supports are stainless steel supports.

18. Anti-foam device according to claim 16, wherein said sliding means are realised through a screwed up collar.

19. Anti-foam device according to claim 14, wherein the length of the portion of each of said sections immersed in said liquid culture medium is in the range from 1 to 10 mm.

20. Anti-foam device according to claim 14, wherein each of said sections has a square or rectangular shape.

21. Anti-foam device according to claim 14, wherein each of said sections is a pierced plate made of a silicone polymer, the thickness of said plate being in the range from 1 to 5 mm.

22. Anti-foam device according to claim 14, wherein the perforations of each of said sections has sharp angles.

23. Anti-foam device according to claim 14, wherein the holes of each of said sections have a square or rectangular shape.

24. Anti-foam device according to claim 23, wherein the size of said square holes is in the range from 1×1 mm to 10×10 mm.

25. Anti-foam device according to claim 14, wherein said hydrophobic material is selected from the group consisting of hydrophobic polymers, and of metallic nets coated with the above mentioned polymers.

26. Anti-foam device according to claim 25, wherein said hydrophobic polymers include silicone, polyamides, polypropylene, polyesters, fluorinated plastomers ans elastomers, synthetic rubber.

27. Anti-foam device according to claim 1, wherein the rotation speed of said perforated plate improving the surface aeration rate of said liquid culture medium is in the range from 10 to 100 rpm.

28. Anti-foam device according to claim 14, wherein the rotation speed of said perforated plate improving the surface aeration rate of said liquid culture medium is in the range from 10 to 100 rpm.

* * * * *